United States Patent
Chatterjee et al.

(10) Patent No.: US 11,337,959 B1
(45) Date of Patent: May 24, 2022

(54) PHARMACEUTICAL COMPOSITION MIX B TO TREAT HEALTH CONDITIONS ASSOCIATED WITH ELEVATED GLUCOSE LEVELS

(71) Applicant: Matthias W Rath, Henderson, NV (US)

(72) Inventors: Madhurima Chatterjee, Santa Clara, CA (US); Matthias W Rath, Aptos, CA (US); Aleksandra Niedzwiecki, Aptos, CA (US); Anna Goc, San Jose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 17/561,971

(22) Filed: Dec. 26, 2021

Related U.S. Application Data

(63) Continuation of application No. 17/378,625, filed on Jul. 16, 2021, now Pat. No. 11,246,855.

(51) Int. Cl.
*A61K 31/07* (2006.01)
*A61K 31/51* (2006.01)
(Continued)

(52) U.S. Cl.
CPC .......... *A61K 31/375* (2013.01); *A61K 31/047* (2013.01); *A61K 31/07* (2013.01); *A61K 31/122* (2013.01); *A61K 31/197* (2013.01); *A61K 31/198* (2013.01); *A61K 31/355* (2013.01); *A61K 31/385* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/575* (2013.01); *A61K 31/593* (2013.01); *A61K 31/7004* (2013.01); *A61K 31/7084* (2013.01); *A61K 31/714* (2013.01); *A61K 33/00* (2013.01); *A61K 33/06* (2013.01); *A61K 33/18* (2013.01); *A61K 33/22* (2013.01);
(Continued)

(58) Field of Classification Search
CPC .... A61K 31/375; A61K 31/51; A61K 31/714; A61K 31/355; A61K 31/593; A61K 31/197; A61K 31/07; A61K 31/455; A61K 33/00; A61K 36/282; A61K 31/385; A61K 31/7004; A61K 31/4415; A61K 31/519; A61K 36/54; A61K 36/82; A61K 33/30; A61K 31/122; A61K 33/06; A61K 33/18; A61K 33/32; A61K 31/525; A61K 36/87; A61K 33/22; A61K 36/61; A61K 31/047; A61K 31/4188; A61K 31/198; A61K 31/575; A61K 36/185; A61K 31/7084
See application file for complete search history.

(56) References Cited

PUBLICATIONS

Maoka, T. (Journal of Natural Medicines 2020;74:1-16) (Year: 2020).*

* cited by examiner

*Primary Examiner* — Ernst V Arnold
(74) *Attorney, Agent, or Firm* — Geeta Kadambi; Riddhi IP LLC

(57) ABSTRACT

A threefold decrease in α-amylase inhibition, increase in insulin secretion and glucose uptake increase by the pharmaceutical composition of several naturally occurring substances and vitamins were observed when compared to the control cells, and a c.a. 1-1.5 fold decrease when compared to the positive control. More specifically Mix B shows significant effect on increased insulin secretion and glucose uptake by cells.

7 Claims, 11 Drawing Sheets

(51) Int. Cl.

| | | |
|---|---|---|
| *A61K 33/00* | (2006.01) | |
| *A61K 33/06* | (2006.01) | |
| *A61K 33/18* | (2006.01) | |
| *A61K 36/54* | (2006.01) | |
| *A61K 36/82* | (2006.01) | |
| *A61K 31/375* | (2006.01) | |
| *A61K 31/714* | (2006.01) | |
| *A61K 31/355* | (2006.01) | |
| *A61K 31/593* | (2006.01) | |
| *A61K 31/197* | (2006.01) | |
| *A61K 31/455* | (2006.01) | |
| *A61K 36/282* | (2006.01) | |
| *A61K 31/385* | (2006.01) | |
| *A61K 31/7004* | (2006.01) | |
| *A61K 31/4415* | (2006.01) | |
| *A61K 31/519* | (2006.01) | |
| *A61K 33/30* | (2006.01) | |
| *A61K 31/122* | (2006.01) | |
| *A61K 33/32* | (2006.01) | |
| *A61K 31/525* | (2006.01) | |
| *A61K 36/87* | (2006.01) | |
| *A61K 33/22* | (2006.01) | |
| *A61K 36/61* | (2006.01) | |
| *A61K 31/047* | (2006.01) | |
| *A61K 31/4188* | (2006.01) | |
| *A61K 31/198* | (2006.01) | |
| *A61K 31/575* | (2006.01) | |
| *A61K 36/185* | (2006.01) | |
| *A61K 31/7084* | (2006.01) | |

(52) U.S. Cl.
CPC ............... *A61K 33/30* (2013.01); *A61K 33/32* (2013.01); *A61K 36/185* (2013.01); *A61K 36/282* (2013.01); *A61K 36/54* (2013.01); *A61K 36/61* (2013.01); *A61K 36/82* (2013.01); *A61K 36/87* (2013.01)

US 11,337,959 B1

PHARMACEUTICAL COMPOSITION MIX B TO TREAT HEALTH CONDITIONS ASSOCIATED WITH ELEVATED GLUCOSE LEVELS

CROSS REFERENCE TO RELATED APPLICATIONS

This application is a continuation of and claims priority to U.S. application Ser. No. 17/378,625 filed on 16 Jul. 2021. The disclosure is hereby incorporated by this reference in their entirety for all of their teachings.

FIELD OF STUDY

This disclosure relates to inhibiting cell entry alpha amylase activity in intestinal cells using a pharmaceutical composition Mix A containing several micronutrients and plant extracts.

BACKGROUND

Hyperglycemia is caused due to many reasons. Micronutrients and, plant extracts and herbal medicines are used are used for treating and preventing diseases. There are no combinations of micronutrients and other medications that solve multiple issues in complicated diseases that raise sugar levels in the body. There is a need for a combination that addresses several issues of systemic disease that raises blood sugar levels to abnormal levels.

SUMMARY

In one embodiment, a pharmaceutical composition for the prevention and treatment of elevated sugar level in humans and other species is disclosed. In one embodiment, a combination of micronutrients and plant extracts to treat health conditions associated with elevated glucose levels.

A pharmaceutical composition for the prevention of elevated sugar level in humans and other species that uses alpha amylase inhibition is disclosed. A pharmaceutical composition for the treatment of elevated sugar level in humans and other species that uses alpha amylase inhibition is disclosed. In one embodiment a composition of micronutrients and plant extracts to treat Diabetes Mellitus and increase uptake of glucose is disclosed.

A pharmaceutical composition for the prevention and treatment of elevated sugar level in humans and other species is disclosed that contains two or more defined formulations of compounds. A pharmaceutical composition for the prevention and treatment of elevated sugar level in humans and other species is disclosed that increases glucose uptake by the cells in the presence and absence of insulin.

A pharmaceutical composition for oral intake at physiological concentration is disclosed. A pharmaceutical composition where two or more of the compounds are chemically bound/covalently linked to each other. A pharmaceutical composition comprising carriers, stabilizers and/or other medically acceptable additives is disclosed.

In one embodiment, plant based and synthetic vitamins, natural seed extracts, trace minerals and minerals, essential nutrients, coenzyme, and amino acids are combined as pharmaceutical composition to treat health conditions associated with elevated glucose levels.

In one embodiment, wherein the vitamins are ascorbic acid (L-ascorbic acid), vitamin E, vitamin B1, vitamin B2, vitamin B3, vitamin B5, vitamin B6, folic acid, vitamin B7, vitamin B12, vitamin A, vitamin K2, vitamin D3, plant extracts are cinnamon extract, green tea extract, grape seed extract, *Artemisia* extract, clove extract, maqui extract, natural carotenoid mix, amino acids are L-Arginine, L-Lysine, minerals are vanadium, magnesium, calcium, chromium, zinc, manganese, potassium, iodine, boron and other essential compounds such as Nicotinamide adenine dinucleotide (NADH), inositol, lipoic acid, silica, and choline.

In one embodiment a pharmaceutical composition comprises of a combination of Mix B and one or more of the following compounds: L-ascorbic acid, vitamin A, vitamin E, vitamin D3, vitamin K2 (as Menaquinone-7), choline, folic acid, calcium, magnesium, potassium, zinc, manganese, boron, iodine, silica, natural carotenoid mix (alpha carotene, lutein, zeaxanthin, cryptoxanthin) and inositol.

In one embodiment, Mix B components in specific range consists of L-ascorbic acid 1-20,000 mg, vitamin E 1-3,000 mg, folic acid 1-3,000 mcg, choline 1-5,000 mg, zinc 1-1,000 mg, magnesium 10-5,000 mg, calcium 10-5,000 mg, inositol 1-15,000 mg, vitamin A 10-25,000 IU vitamin K2 0.01-100 mg, boron 0.01 mg-20 mg, vitamin D3 20-10,000 IU, iodine 0.01 mg-2 mg, silica 1-2,000 mg, natural carotenoid mix 0.01-1,000 mg, manganese 0.01-50 mg, and potassium 1-10,000 mg.

The said combinations can be altered to have more or less components or micronutrients. There may be addition of different forms of ascorbate such as magnesium ascorbate, calcium ascorbate, ascorbyl palmitate, ascorbyl phosphate, sodium ascorbyl phosphate or another form of L-ascorbate in combination or for substitution as well. They may be a combination of several micronutrients that are disclosed to form a pharmaceutical composition. The micronutrient may be used once or multiple times as a dosage in a day to prevent and treat Diabetes Mellitus in a mammal and/or glucose lowering effects for other metabolic diseases. The combination of Mix A, Mix B and vitamin D and vitamin K2 as mix is used for treating diabetes mellitus 1 and diabetes mellitus 2 by increasing the glucose uptake and increasing the insulin production.

BRIEF DESCRIPTION OF FIGURES

Example embodiments are illustrated by way of example and not limitation in the figures of the accompanying drawings, in which like references indicate similar elements and in which.

Figure 1:
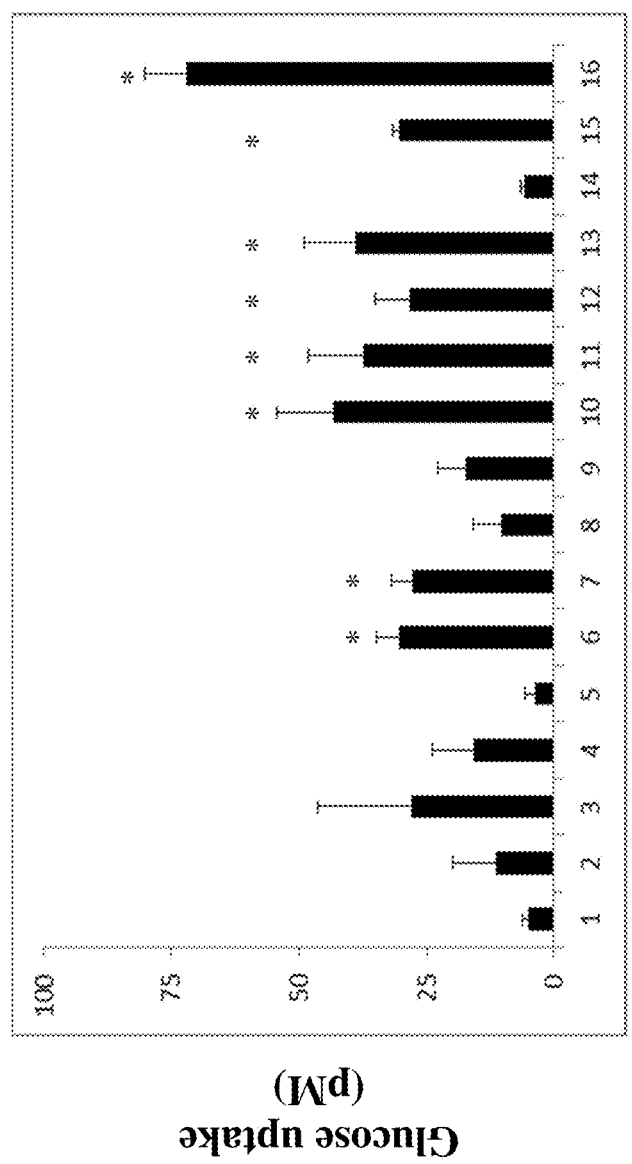
FIG. 1. In vitro uptake of 2-DG (glucose derivative) in IEC-6 intestinal cells stimulated with different individual micronutrients and plant extracts (0.0001-2 µg/ml) and their mixture for 24 h at 37° C.

Other features of the present embodiments will be apparent from the accompanying drawings and from the detailed description that follows.

DETAILED DESCRIPTION

Several diseases and life style conditions raise blood glucose levels. Hyperglycemia leads to other complications and even organ failure in long run. Some diseases, but not limited, that cause hyperglycemia are Pancreatitis (inflammation of the pancreas), Pancreatic cancer, Hyperthyroidism (overactive thyroid gland), Cushing's syndrome (elevated blood cortisol level), unusual tumors that secrete hormones, including glucagonoma, pheochromocytoma, or growth hormone-secreting tumors, Severe stresses on the body, such as heart attack, stroke, trauma, or severe illnesses, can temporarily lead to hyperglycemia and taking certain medications, including prednisone, estrogens, beta-blockers, statins, glucagon, oral contraceptives, phenothiazine's, and others, can elevate blood glucose levels.

Diabetes is a chronic disease characterized by hyperglycemia, and is categorized into two types: Type I Diabetes Mellitus (T1DM) and Type II Diabetes Mellitus (T2DM). In T1DM, b-cells of the pancreas are damaged, limiting insulin supply to the circulation. Patients will be fully dependent on exogenous insulin administration for existence. Contrarily, T2DM has been observed in majority of diabetic patients (85%) and results in peripheral insulin resistance, thereby results in decreased insulin sensitivity to the skeletal muscles, adipose tissues and liver. Different categories of antidiabetic medications are there in the market for the remedial action, which includes insulin analogues, sulphonylureas, biguanides, dipeptidyl peptidase-4 inhibitors, thiazolidiones, α-glucosidase inhibitors etc., where the mechanism of counteracting this increased glucose level is different for different categories. However, long term treatment and side effect of the available hypoglycemic medications leading towards huge demand for efficacious, decreased side effects and affordable and safe agents for the treatment of diabetic condition (Choudhry 2018).

In the instant disclosure we combined a group of plant based and synthetic vitamins, natural seed extracts, trace minerals and minerals, essential nutrients, coenzyme, and amino acids are combined as pharmaceutical composition to treat health conditions associated with elevated glucose levels. We used different permutations and combinations for lowering glucose levels by inhibiting glucose uptake and amylase inhibition in different muscles and cells. Various individual mix either in combination or individually is used for treating diabetes mellitus 1 and diabetes mellitus 2 and other metabolic disorders by increasing the glucose uptake and increasing the insulin production.

Table 1: The table shows various combination of Mix A, Mix B and Mix C that were used for reducing glucose uptake:

| Mix A | |
| --- | --- |
| L-Ascorbic acid | 1-20,000 mg |
| Vitamin E | 1-3,000 mg |
| Folic acid | 1-3,000 mcg |
| Vitamin B1 | 1-3,000 mg |
| Vitamin B2 | 1-2,000 mg |
| Vitamin B3 | 1-3,000 mg |
| Vitamin B5 | 1-20,000 mg |
| Vitamin B6 | 1-1,000 mg |
| Vitamin B7 (biotin) | 1-20,000 mg |
| Vitamin B12 | 0.01-2 mg |
| Lipoic Acid | 1-5,000 mg |
| Choline | 1-5,000 mg |
| Cinnamon extract | 1-10,000 mg |
| Zinc | 1-1,000 mg |
| Vanadium | 10-1,000 mcg |
| L-Arginine | 1-20,000 mg |
| L-Lysine | 1-20,000 mg |
| Magnesium | 10-5,000 mg |
| Calcium | 10-5,000 mg |
| Chromium$^{(+3)}$ | 1-1,500 mcg |
| Inositol | 1-15,000 mg |
| Grape Seed Extract | 1-8,000 mg |
| Green Tea extract | 1-20,000 mg (or 1-5,000 mg as EGCG) |

| Mix B | |
| --- | --- |
| L-Ascorbic acid | 1-20,000 mg |
| Vitamin E | 1-3,000 mg |
| Folic acid | 1-3,000 mcg |
| Choline | 1-5,000 mg |
| Zinc | 1-1,000 mg |
| Magnesium | 10-5,000 mg |
| Calcium | 10-5,000 mg |
| Inositol | 1-15,000 mg |
| Vitamin A | 10-25,000 IU |
| vitamin K2 | 0.01-100 mg |
| Boron | 0.01 mg-20 mg |
| Vitamin D3 | 20 IU-10,000 IU |
| Iodine | 0.01 mg-2 mg |
| Silica | 1-2,000 mg |
| Natural carotenoid mix | 0.01-1,000 mg |
| Manganese | 0.01-50 mg |
| Potassium | 1-10,000 mg |

| Mix C | |
| --- | --- |
| Vitamin C (L-ascorbic acid) | 1-20,000 mg |
| Vitamin E | 1-3,000 mg |
| Vitamin B1 | 1-3,000 mg |
| Vitamin B2 | 1-2,000 mg |
| Vitamin B3 | 1-3,000 mg |
| Vitamin B5 | 1-20,000 mg |
| Vitamin B6 | 1-1,000 mg |
| Vitamin B7 | 1-20,000 mg |
| Vitamin B12 | 0.01-2 mg |
| Lipoic Acid | 1-5,000 mg |
| Choline | 1-5,000 mg |
| Cinnamon extract | 1-10,000 mg |
| Zinc | 1-1,000 mg |
| Magnesium | 10-5,000 mg |
| Chromium$^{(+3)}$ | 1-1,500 mcg |
| Inositol | 1-15,000 mg |
| Artemisia Extract | 1-2,000 mg |
| NADH | 0.1-20,000 mg |
| Clove Extract | 0.1-2,000 mg |
| Maqui Extract | 0.1-500 mg |

The concentrations shown are physiological concentrations for human use. These are packaged in several formats for daily consumption.

Materials and Methods

Test compounds. The following compounds, with the purity between 90%-98% according to the manufacturer, were obtained from Sigma (St. Louis, Mo.): vitamin C, lipoic acid, NADH and human insulin. The compounds such as vitamin B-complex, vitamin E, magnesium, chromium, zinc, inositol, and choline, with the purity between 90%-98% according to the manufacturer, were purchased from Powder City (York, Pa.). Maqui extract, clove extract, and cinnamon extract with the purity between 97%-99% according to the manufacturer, was from Monterey Bay Spice (Watsonville, Calif.). Intestinal epithelial cell line 6 (IEC-6), pancreatic Beta TC-6 insulin secreting cell line and rat skeletal muscle cell line were from ATCC (Manassas, Va.). Immortalized microglial cell line (IMG) isolated from the brains of adult mice were purchased from Kerafast. Assay kits used: Glucose Uptake-Glo™ Assay kit from Promega, Insulin Elisa: Mouse Insulin ELISA Kit from Biovision, Alamar Blue Cell Viability reagent from ThermoFisher, AGE: Glycated Bovine Serum Albumin (BSA) from Abcam.

Sample preparations: All cells were grown in Dulbecco's Modified Eagle Medium (DMEM) supplemented with Fetal Bovine Serum (FBS) and Penicillin-Streptomycin. Mix A and Mix B were solubilized in 0.1N Hydrochloric Acid according to Pharmacopeia protocols. Briefly, the tablets were crushed and shaken overnight at 37° C. in 0.1N HCl. Solution was filter sterilized and frozen in aliquots. Vitamin D+K2 was solubilized in DMSO and frozen in aliquots. It was filter sterilized after dilution with media before adding to cells. Ascorbic Acid solution was prepared freshly every time in DMSO. It was filter sterilized after dilution with media before adding to cells.

In vitro glucose uptake assay: The assay was performed according to manufactures' protocol. Briefly, intestinal L6 cell line cells were seeded and grown to confluency in white 96 well plates in culture medium containing 10% FBS (serum). After treating with various nutrients with or without insulin cells were starved by incubating in DMEM without glucose and serum. Samples were processed using Glucose Uptake Assay kit according to manufacturer's protocol that uses the glucose analog 2-deoxyglucose (2-DG) to detect and quantify glycose uptake in cells. Luminescence was measured by a Tecan luminometer. 4 repetitions were performed for each treatment when testing individual components and 3 repetitions when testing mixes.

In vitro α-Amylase inhibition: The following assay was performed according to Shekib et al. Plant Foods Human Nutr. 1988; 38:325-332. Alpha amylase inhibitory activity was based on the starch-iodine method. Briefly, 1 ml substrate-potato starch (1% w/v), 1 ml of drug solution (Acarbose std. drug of 50m/m1), individual ingredients or mix of them, 1 ml of alpha amylase enzyme (1% w/v), and 2 ml of acetate buffer (0.1 M, 7.2 pH) was added. The above mixture was incubated for 1 hr. Then 0.1 ml iodine-iodide indicator (635 mg iodine and 1 g potassium iodide in 250 ml distilled water) was added in the mixture. Absorbance was taken at 565 nm in UV-Visible spectroscopy. All the tests were performed in triplicate. Means and standard deviations were determined for all experiments and Student's t test analysis was used to determine significant differences. Statistical analysis was performed by two-sample paired t-test using GraphPad statistical software.

Insulin ELISA: Pancreatic cells were seeded and grown to confluency in 96 well plates. They were treated with nutrient mixes for 48 hours. Cell supernatant was centrifuged to remove sediments and the resulting supernatant was assayed using the Insulin ELISA kit according to manufacturer instructions. 3 repetitions were performed for each treatment.

Cell protection from advanced glycation products: IMG cells were seeded and grown to confluency in clear 96 well plates. They were treated with nutrient mixes together with 1 mg/ml AGE in DMEM with 1% FBS. After 24 hours, cells were washed with Phosphate-buffered saline (PBS) and Alamar Blue assay was performed to test cells viability. 6 repetitions were performed for each treatment.

Results

FIG. 1. In vitro uptake of 2-DG (glucose derivative) in IEC-6 intestinal cells stimulated with different micronutrients and plant extracts (0.0001-2 µg/ml) for 24 h at 37° C. Values shown are mean±standard deviation (n=4); Value significantly different from corresponding control at * $p<0.001$ compared to control. Approximately a 7 fold increase in glucose uptake by IEC-6 intestinal cells treated with the composition of 14 naturally occurring substances was observed when compared to the control cells, and a c.a. 1-2 fold increase when compared to the most stimulating glucose uptake individual compounds compared to controls such as vitamin C, vitamin E, vitamin b-complex, magnesium, chromium, zinc, NADH, lipoic acid, cinnamon extract, *artemisia* extract, and maqui extract, and as their Mix C, respectively. The figure legend and their numbers are as follows: 1. Control, 2. Vitamin C, 3. Vitamin E, 4. Vitamin B-complex, 5. Magnesium, 6. Chromium, 7. Zinc, 8. Inositol, 9. Choline, 10. NADH, 11. Lipoic acid, 12. Cinnamon extract, 13. *Artemisia* extract, 14. Clove extract, 15. Maqui extract, and 16. Mix.

Figure 2:
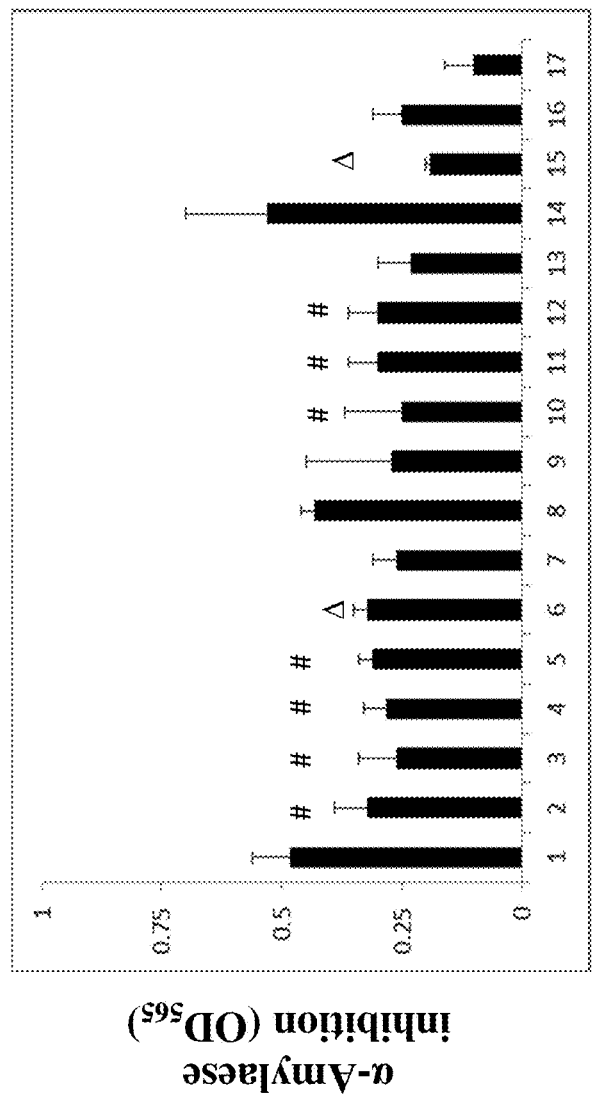
FIG. 2. In vitro α-Amylase inhibition by different micronutrients and plant extracts (5-20 µg/ml) and their mixture after 24 h.

FIG. 2. In vitro α-Amylase inhibition by different micronutrients and plant extracts (5-20 µg/ml) after 24 h. Values shown are mean±standard deviation (n=4); value significantly different from corresponding control at # $p<0.05$, A $p<0.01$, * $p<0.001$ compared to control. Approximately a 3 fold decrease in α-amylase inhibition by the composition of 14 naturally occurring substances was observed when compared to the control cells, and a c.a. 1-1.5 fold decrease when compared to the positive control. The individual micronutrients that were tested along with control and positive control (Acarbose) were vitamin C, vitamin E, vitamin b-complex, magnesium, chromium, zinc, NADH, lipoic acid, cinnamon extract, *artemisia* extract, and maqui extract, and their mix C respectively. The figure legends and their numbers are as follows: 1. Control, 2. Positive control (Acarbose), 3. Vitamin C, 4. Vitamin E, 5. Vitamin B-complex, 6. Magnesium, 7. Chromium, 8. Zinc, 9. Inositol, 10. Choline, 11. NADH, 12. Lipoic acid, 13. Cinnamon extract, 14. *Artemisia* extract, 15. Clove extract, 16. Maqui extract, 17. Mix C.

Figure 3:
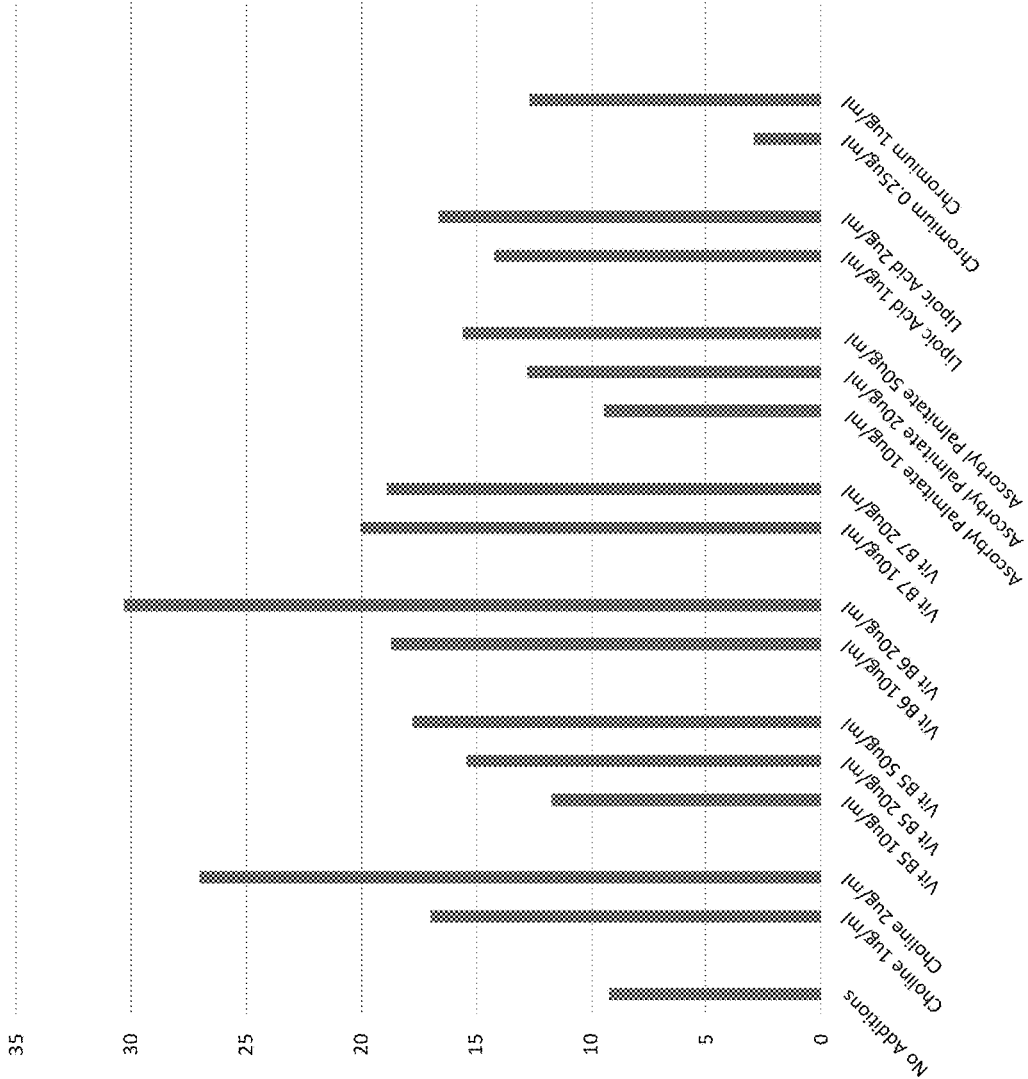
FIG. 3 shows glucose uptake by IEC-6 intestinal cells using individual micronutrients applied at different concentrations.
Figure 4:
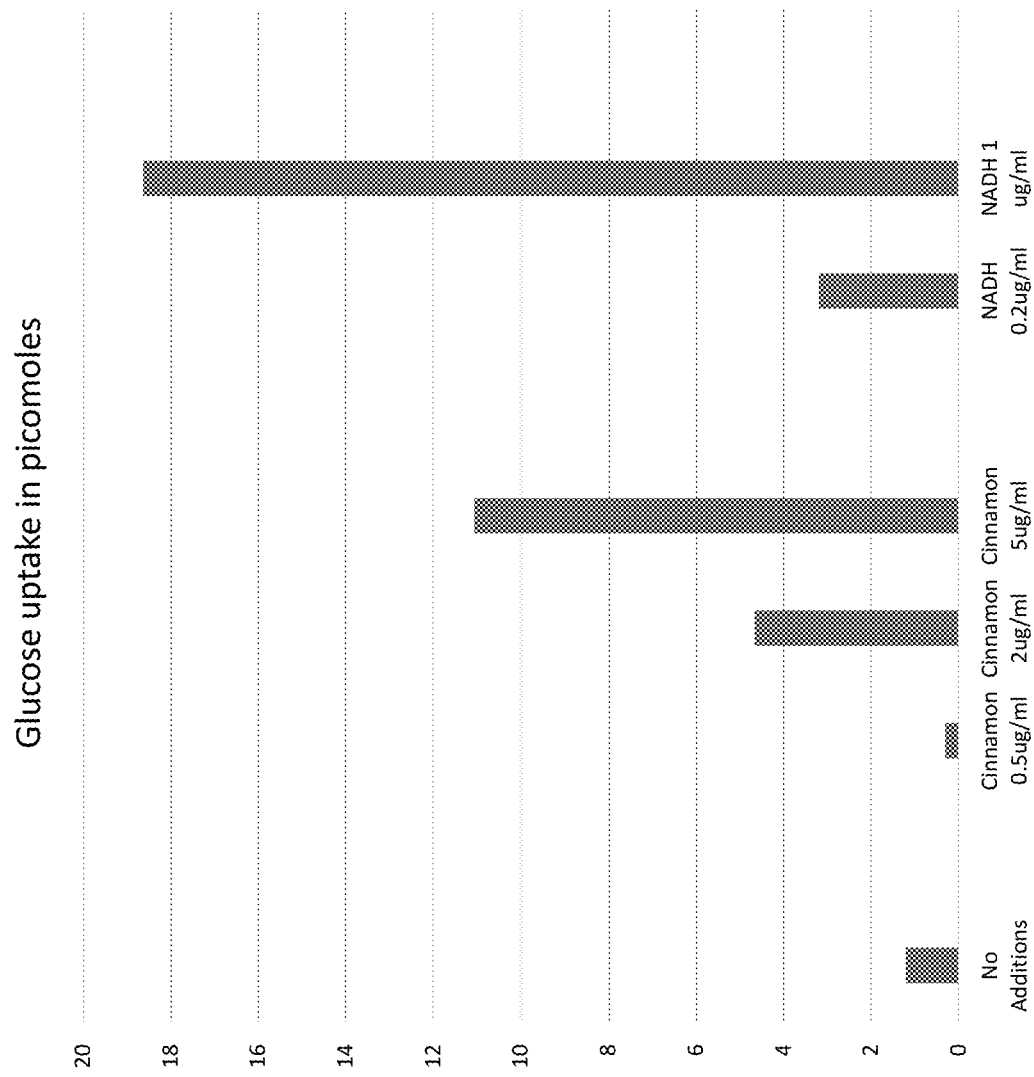
FIG. 4 shows glucose uptake activity by IEC-6 intestinal cells using cinnamon and NADH at different concentrations.
Figure 5:
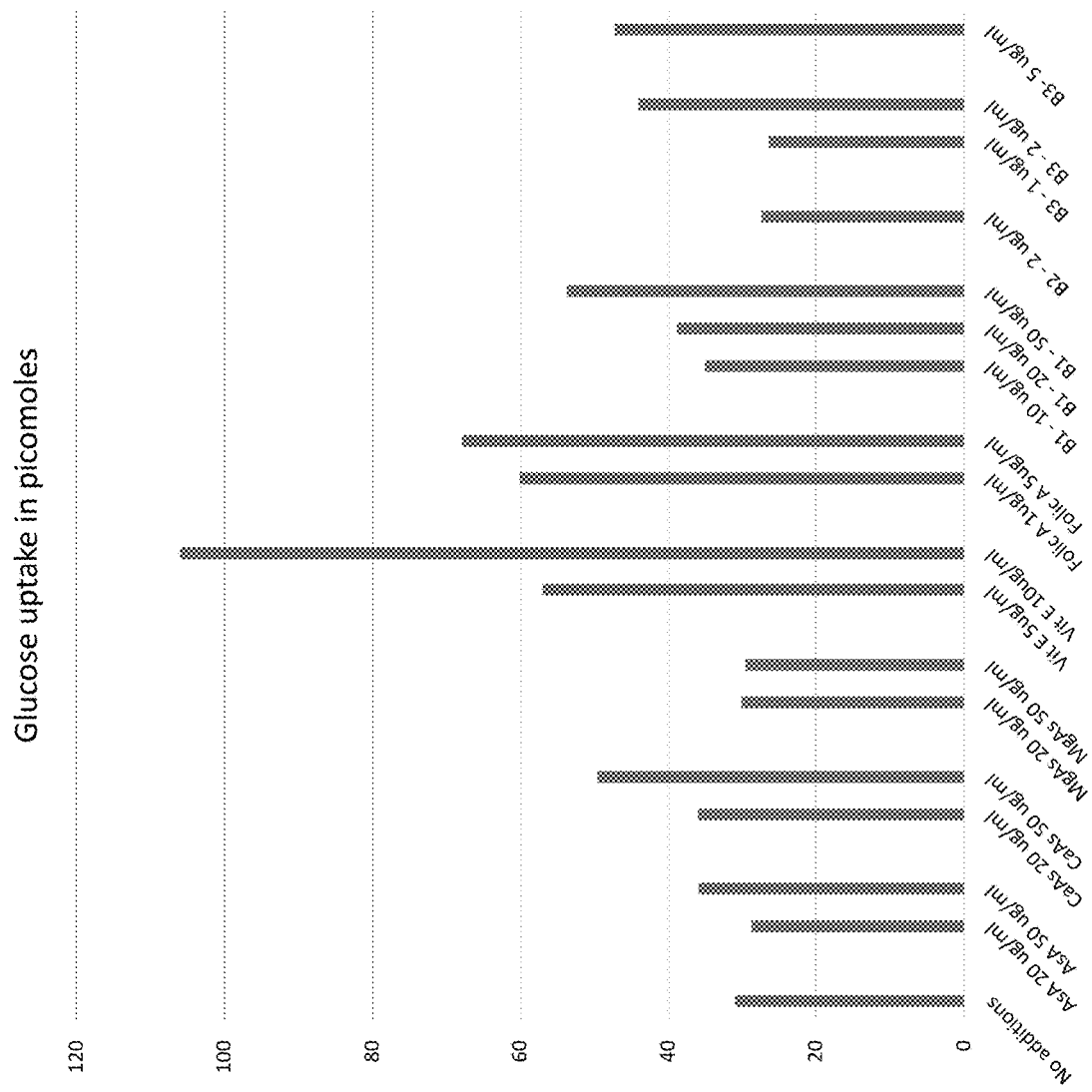
FIG. 5 shows the effects of various vitamins and ascorbic acid applied at different concentrations on glucose uptake by IEC-6 intestinal cells.

FIG. 3 shows concentration dependent effects of individual compounds: choline, vitamin B5, Vitamin B6, Vitamin B7 (biotin), ascorbyl palmitate, lipoic acid and chromium on glucose uptake by IEC-6 cells. FIG. 4 shows concentration dependent effects of cinnamon and NADH on glucose uptake by IEC-6 cells. FIG. 5 shows concentration dependent effects of individual compounds: ascorbic acid, calcium ascorbate, magnesium ascorbate, vitamin E, Folic acid, vitamin B1, Vitamin B2 and, Vitamin B3 on glucose uptake by IEC-6 cells.

Figure 6:
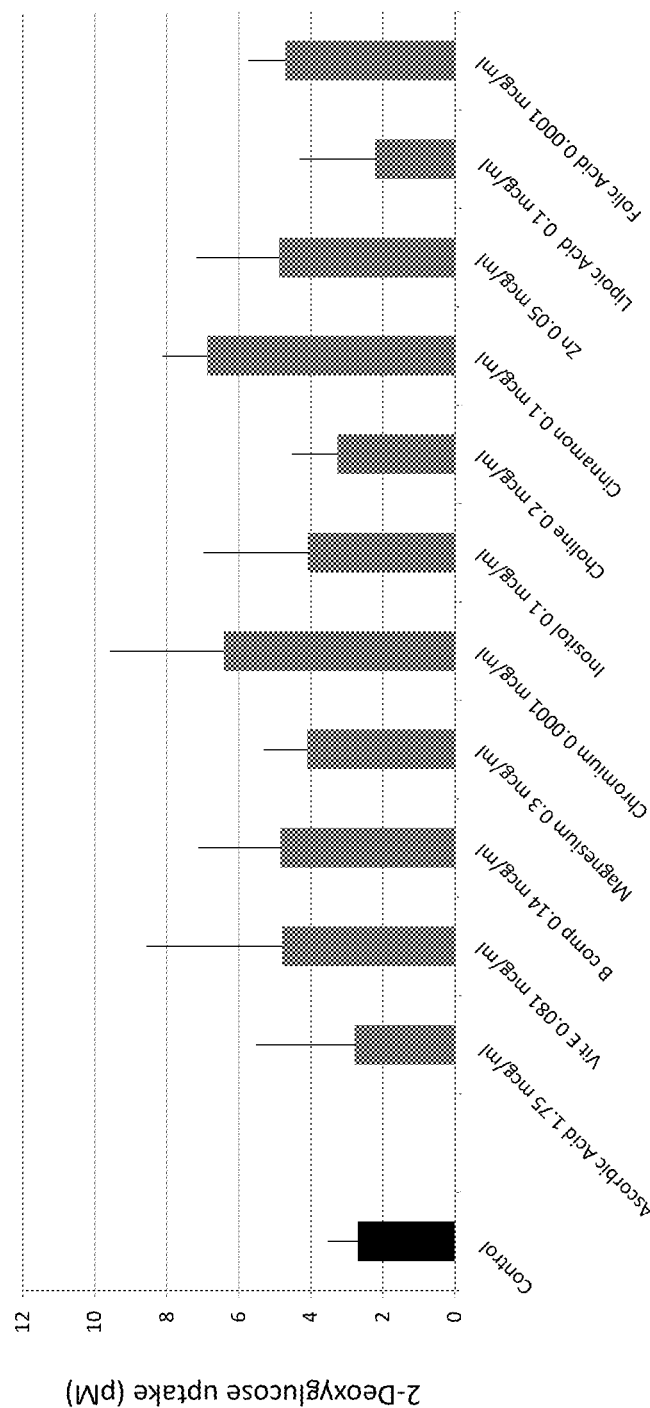
FIG. 6 shows the effects of individual compounds and two natural compound mixtures on glucose uptake by skeletal muscle cells.
Figure 7:
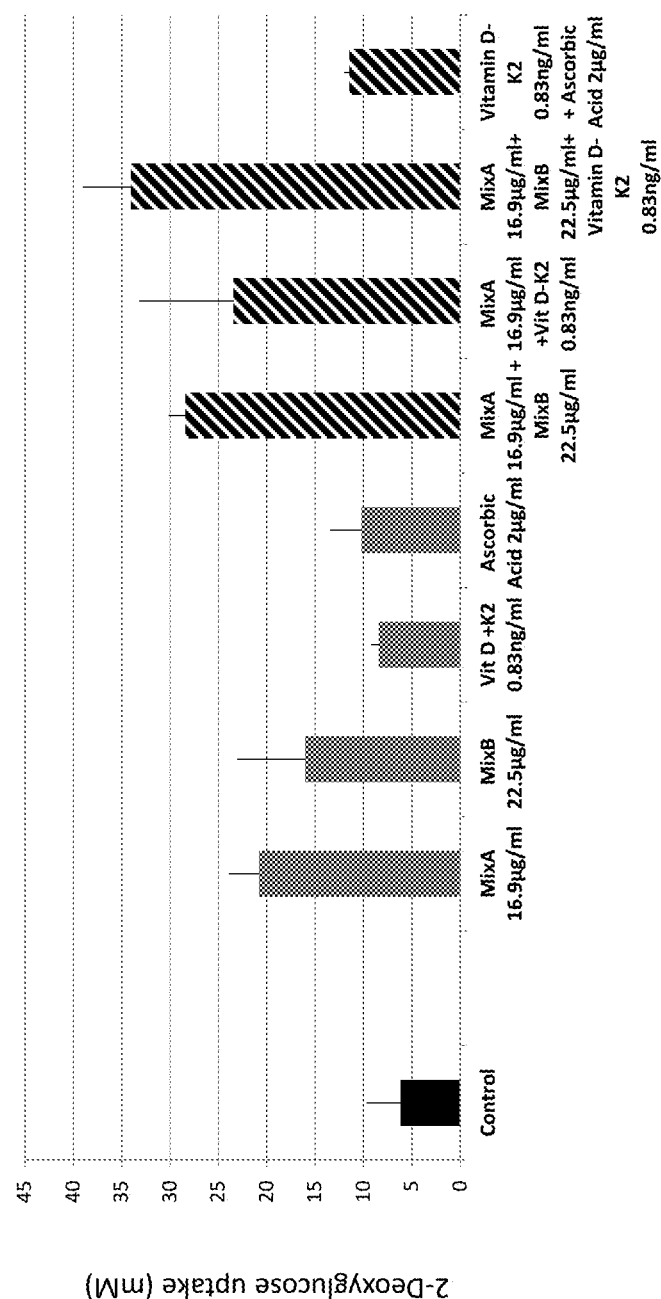
FIG. 7 shows the effects of select pharmaceutical compositions administered individually and in different combinations on glucose uptake by skeletal muscle cells.

FIG. 6. In vitro uptake of 2-DG (glucose derivative) in skeletal muscle cells exposed to different micronutrients and plant extracts (0.0001-2 µg/ml) for 24 h at 37° C. Values shown are mean±standard deviation (n=4); The highest stimulating effect on glucose uptake by individual compounds compared to controls was observed with cinnamon (0.1 ug/ml) and chromium (0.0001 ug/ml). FIG. 7 shows effects of specific compositions of pharmaceutical compounds and their combinations on uptake of 2-DG (glucose derivative) in skeletal muscle cells. Values shown are mean±standard deviation (n=4). A composition of Mix A was the most effective in stimulating glucose uptake compared to Mix B, ascorbic acid and a combination of Vitamin D+K2 and. The glucose uptake stimulating effects further increased to 550% compared to control when the Mix A, Mix B and vitamin D+K2 were combined together.

Figure 8:
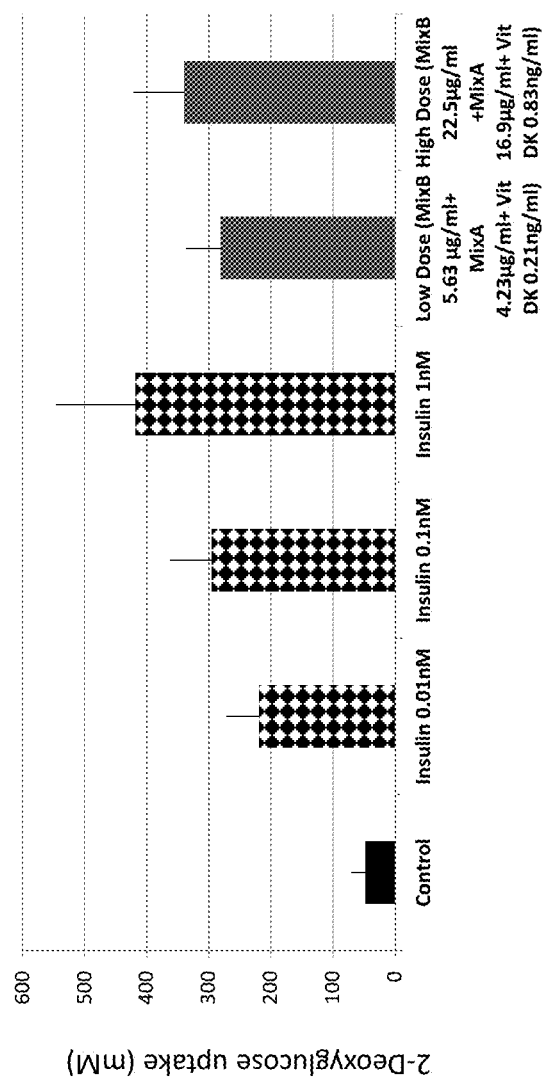
FIG. 8 shows the effects of select pharmaceutical compositions administered in different combinations on glucose uptake by skeletal muscle cells in comparison to the effects of insulin.

FIG. 8 shows the effects of combinations of different formulations on glucose uptake in skeletal muscle cells compared to insulin alone. Values shown are mean±standard deviation (n=4). Insulin showed concentration dependent increase in glucose uptake by the cells. The stimulatory effect of insulin at 0.01 nm concentration was comparable to the increase in glucose uptake obtained in the presence of a high dose combination of Mix A, Mix B and Vitamin D+K2 without insulin present.

Figure 9:
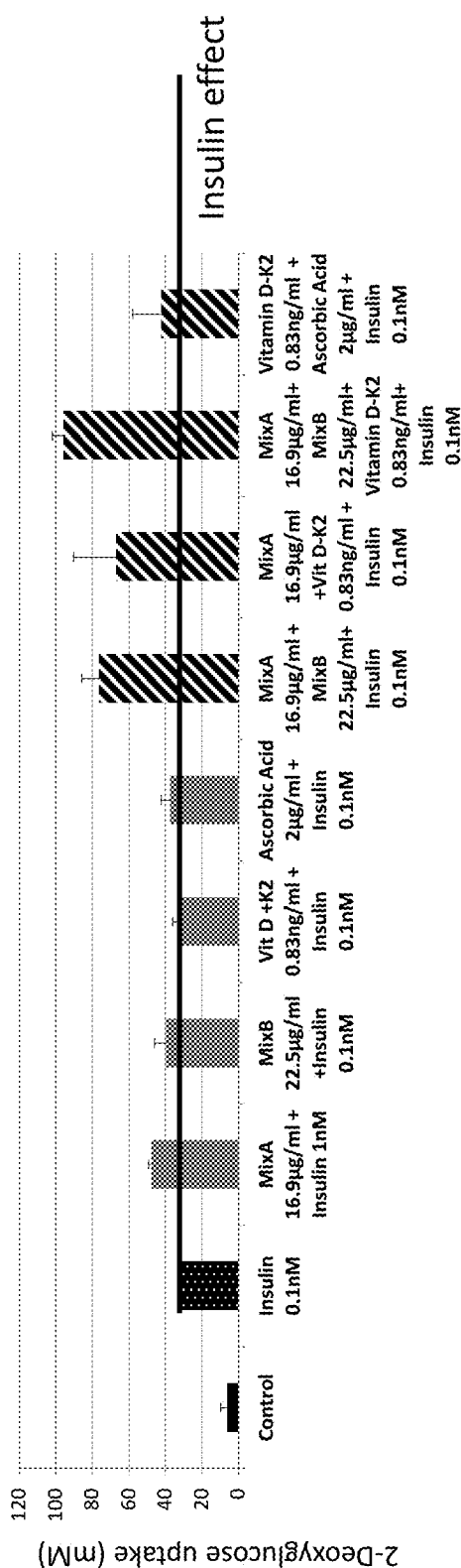
FIG. 9 shows the effects of select pharmaceutical compositions administered individually and in different combinations on glucose uptake by skeletal muscle cells in the presence of insulin.

FIG. 9 shows the effects of co-administration of different pharmaceutical formulations with insulin on glucose uptake in skeletal muscle cells. Values shown are mean±standard deviation (n=4). In the presence of insulin, both Mix A and Mix B applied individually had stimulatory effect on glucose uptake by the cells compared to control and insulin alone. Further increase in glucose uptake by the cells was observed by using different combinations of these formulations. A combination of Mix A, Mix B and vitamin D+K2 showed maximum stimulating effect on glucose uptake and equaled 306% when compared to insulin alone and 1545% when compared to control.

Figure 10:
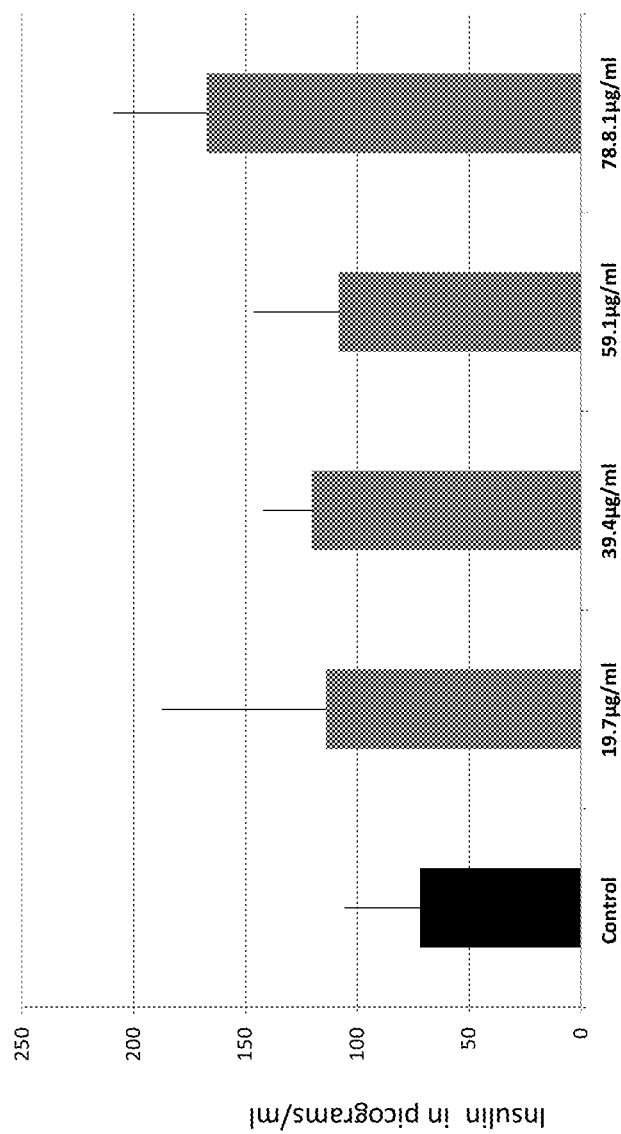
FIG. 10 shows the effects of the combination of three separate pharmaceutical formulas on insulin secretion by human pancreatic cells.

FIG. 10 shows the effects of a combination of three pharmaceutical compositions (Mix A, Mix B and Vitamin D+K2) on insulin secretion by human pancreatic cells. The results show concentration dependent increase in insulin secretion in pancreatic cells from 72 pg/ml in control to 167 pg at the highest concentration of the formulas used in the experiment (78.8 ug/ml).

Figure 11:
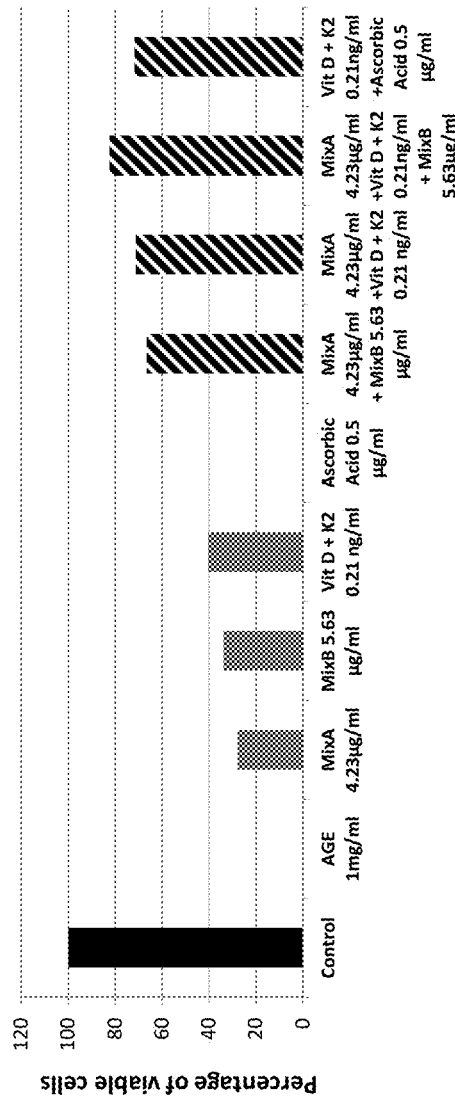
FIG. 11 shows the effects of three formulations of pharmaceutical compounds used individually and various combinations on protection of glial cells against damage by high glycation products (AGE).

FIG. 11 shows the effects of pharmaceutical compositions applied individually and in combinations on protecting glial cells against damage by high glycation products (AGE). The results show that the most protection of cells against AGE induced damage could be achieved by using the combination of Mix A, together with Mix B and Vitamin D+K2.

Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, pharmaceutical micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose, L-Leucine and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, *Stevia*, orange peel, citric acid and tartaric acid.

When a liquid drug product for oral administration is prepared, pharmaceutical micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with pharmaceutical micronutrient composition.

Formulations containing pharmaceutical micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing pharmaceutical micronutrient composition can be added to the extended-release system by means of either applying an immediate-release layer on top of the extended release core; using coating or compression processes, or in a multiple-unit system such as a capsule containing extended- and immediate-release beads.

When used with respect to a pharmaceutical micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the pharmaceutical micronutrient composition is released over a period of time in a controlled manner from a formulation. Types of sustained release formulations include liposomes, drug-loaded biodegradable microspheres and pharmaceutical micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a pharmaceutical micronutrient composition with a selected coating material. The pharmaceutical micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant pharmaceutical micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

Certain pharmaceutical micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, pharmaceutical micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens and Freund's adjuvant may also be used to produce water-in-oil emulsions of immunogens.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical micronutrient compositions described herein are formulated in a manner such that said compositions will be delivered to a mammal in a therapeutically effective amount, as part of a prophylactic, preventive or therapeutic treatment to overcome the infection caused by corona viruses (irrespective of the type).

In certain embodiments, the dosage of the pharmaceutical micronutrient compositions, which may be referred to as therapeutic composition provided herein, may be determined by reference to the plasma concentrations of the therapeutic composition or other encapsulated materials. For example, the blood samples may be tested for their immune response to their corresponding viral load or lack thereof.

The therapeutic pharmaceutical micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject pharmaceutical micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject pharmaceutical micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the pharmaceutical micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

What is claimed is:

1. A pharmaceutical composition consisting of:
A L-ascorbic acid, vitamin A, vitamin E, vitamin D3, vitamin K2, choline, folic acid, calcium, magnesium, potassium, zinc, manganese, boron, iodine, silica, inositol and a natural carotenoid mix consisting of alpha carotene, lutein, zeaxanthin and cryptoxanthin; to form a Mix B and the Mix B is formulated as a tablet, coated tablet, capsule, pill, lozenges, emulsion, pastilles, suppository, paste and injectable solution for mammalian consumption.

2. The pharmaceutical composition of claim 1, wherein a specific range for the pharmaceutical composition consists of the L-ascorbic acid 1-20,000 mg, vitamin E 1-3,000 mg, folic acid 1-3,000 mcg, choline 1-5,000 mg, zinc 1-1,000 mg, magnesium 10-5,000 mg, calcium 10-5,000 mg, inositol 1-15,000 mg, vitamin A 10-25,000 IU vitamin K2 0.01-100 mg, boron 0.01 mg-20 mg, vitamin D3 20-10,000 IU, iodine 0.01 mg-2 mg, silica 1-2,000 mg, natural carotenoid mix 0.01-1,000 mg, manganese 0.01-50 mg, and potassium 1-10,000 mg.

3. The pharmaceutical composition of claim 1 increases a glucose uptake in skeletal muscle cells.

4. The pharmaceutical composition of claim 2 protects a glial cell against damage by an Advanced Glycated BSA (AGE).

5. The pharmaceutical composition of claim 2 increases a glucose uptake in skeletal muscle cells.

6. The pharmaceutical composition of claim 2 increases secretion of insulin by a pancreatic cell in the presence of the said pharmaceutical composition.

7. The pharmaceutical composition of claim 2 is used for treating diabetes mellitus 1 and diabetes mellitus 2 by increasing a glucose uptake and increasing an insulin production.

\* \* \* \* \*